United States Patent [19]  [11]  4,069,268
Siskin et al.  [45]  Jan. 17, 1978

[54] REGENERATION OF METAL HALIDE CATALYSTS VIA HALOGENATION

[75] Inventors: Michael Siskin, Maplewood, N.J.; Ronald J. Gillespie, Dundas, Canada

[73] Assignee: Exxon Research & Engineering Co., Linden, N.J.

[21] Appl. No.: 628,587

[22] Filed: Nov. 4, 1975

[51] Int. Cl.² .......... C07C 5/28; C07C 3/54; C10G 35/06; B01J 27/32

[52] U.S. Cl. .......... 260/666 P; 252/415; 260/666 R; 260/671 R; 260/683.2; 260/683.47; 260/683.68; 260/683.7; 260/683.74; 208/134; 423/62; 423/64; 423/492

[58] Field of Search .......... 252/415; 260/666 P, 260/668 A, 671 R, 674 R, 683.47, 683.58, 683.66, 683.68, 683.7, 683.74, 683.75; 423/62, 64, 492; 23/294; 208/134

[56] References Cited

U.S. PATENT DOCUMENTS

| 2,280,748 | 4/1942 | Calhoun | 260/683.75 |
|---|---|---|---|
| 2,411,054 | 11/1946 | Pevere | 260/683.53 |
| 2,733,219 | 1/1956 | Bloch | 260/683.75 |
| 2,816,815 | 12/1957 | Ruhoff et al. | 423/62 |
| 2,934,426 | 4/1960 | Mayer | 23/294 |
| 2,943,126 | 6/1960 | Schriesheim | 260/683.53 |
| 3,011,866 | 12/1961 | Gibson | 423/62 |
| 3,129,190 | 4/1964 | Hill | 252/442 |
| 3,320,023 | 5/1967 | George | 423/62 |
| 3,809,728 | 5/1974 | Kemp et al. | 260/683.68 |
| 3,852,184 | 12/1974 | Siskin et al. | 260/666 P |
| 3,880,945 | 4/1975 | Kramer et al. | 260/683.75 |
| 3,948,761 | 4/1976 | Siskin et al. | 260/683.68 |

Primary Examiner—Winston A. Douglas
Assistant Examiner—P. E. Konopka
Attorney, Agent, or Firm—John W. Ditsler

[57] ABSTRACT

Deactivated or partially deactivated hydrocarbon conversion catalysts comprising (a) one or more Lewis acids of the formula $MX_n$ where M is a component selected from Group IIIA, IVB, V, VIB or VIII Elements of the Periodic Table or their mixtures, X is a halogen, and n is the atomic ratio of halogen to M and varies from 1 to 8, and (b) a strong Bronsted acid, may be regenerated by contacting said catalysts with a halogen selected from the group consisting of fluorine or chlorine. If a portion of the catalyst has been hydrolyzed, the catalyst may be regenerated via halogenation as above or by contact with a hydrogen halide selected from the group consisting of hydrogen fluoride or hydrogen chloride and then fluorine. The preferred Lewis acid is a metal halide, preferably tantalum pentafluoride, niobium pentafluoride or mixtures thereof. The preferred Bronsted acid is a hydrogen halide, preferably hydrogen fluoride.

17 Claims, No Drawings

REGENERATION OF METAL HALIDE CATALYSTS VIA HALOGENATION

BACKGROUND OF THE INVENTION

1. Field of the Invention

The present invention relates to a process for regenerating a catalyst of the type used in hydrocarbon conversion processes. More particularly, this invention relates to a process for regenerating a catalyst that has become deactivated or partially deactivated by the formation of stable, catalytically inert complexes during contact with a hydrocarbon feedstock, said catalyst comprising (a) one or more Lewis acids of the formula $MX_n$ where M is a component selected from Group IIIA, IVB, V, VIB or VIII Elements of the Periodic Table or their mixtures, X is a halogen, n is the atomic ratio of halogen to M and varies from 1 to 8, and (b) a strong Bronsted acid, by contacting said catalyst with either a halogen or a hydrogen halide and fluorine.

2. Description of the Prior Art

It is well known in the prior art that the activity of Friedel Craft's type hydrocarbon conversion catalysts declines gradually due to the accumulation of various contaminants or poisons, such as compounds of carbon, sulfur, nitrogen, oxygen, metals, water and the like, until the catalysts cease to exhibit an economic activity. In such cases, depending upon economic factors, the catalyst may be replaced or regenerated to restore desired activity levels.

Several methods have been suggested for regenerating Friedel-Craft's hydrocarbon conversion catalysts via halogenation. For example, U.S. Pat. No. 2,709,688 teaches the regeneration of spent aluminum or zirconium fluoride catalysts by contact with chlorine trifluoride. U.S. Pat. No. 2,113,028 discloses the regeneration of spent double halide catalysts by contacting same with a halogen. In addition, U.S. Pat. No. 2,488,744 teaches the removal of metal contaminants from a silica-alumina cracking catalyst using a mixture of hydrogen chloride and chlorine. U.S. Pat. No. 3,369,862 discloses that stable, catalytically inert hexafluoroantimonic acid complexes can be decomposed to antimony trifluoride and lower molecular weight hydrocarbons, with the antimony trifluoride then being converted to antimony pentafluoride or directly to hexafluoroantimonic acid by treatment with florine or chlorine and hydrogen fluoride. U.S. Pat. No. 3,809,728 teaches regenerating a supported hydrogen fluoride-antimony pentafluoride catalyst with liquid hydrogen fluoride and then recontacting the catalyst support with a liquid solution of hydrogen fluoride antimony pentafluoride. However, none of the foregoing prior art discloses a method for regenerating the catalyst system described hereinafter using a halogen or a hydrogen halide and fluorine.

SUMMARY OF THE INVENTION

Now in accordance with the present invention, it has been discovered that a deactivated or partially deactivated hydrocarbon conversion catalyst comprising (a) one or more Lewis acids of the formula $MX_n$ where M is a component selected from Group IIIA, IVB, V, VIB, or VIII Elements of the Periodic Table or their mixtures, X is a halogen, n is the atomic ratio of halogen to M and varies from 1–8, preferably from 3–8, and (b) a strong Bronsted acid, may be regenerated by contacting same with a halogen selected from the group consisting of fluorine or chlorine. If at least a portion of the deactivated catalyst has been degraded by hydrolysis and converted to a metal oxyhalide or an oxide, such as might occur due to the presence of water or some basic material, the catalyst may be regenerated by direct halogenation as above or by contact with a hydrogen halide selected from the group consisting of hydrogen fluoride or hydrogen chloride followed by fluorination. The preferred halogen is fluorine while the preferred hydrogen halide is hydrogen fluoride. The halogen reacts with the contaminants and/or degraded catalyst that deactivate the catalyst to form volatile halogenated derivatives. Similarly, any metallic contaminants present in the deactivated catalyst will be converted to their halogen derivatives.

Thus, when at least a portion of a deactivated or partially deactivated hydrocarbon conversion catalyst comprising a Lewis acid and a Bronsted acid is contacted with a halogen or hydrogen halide under the conditions as defined above, there results, in general, a gas phase comprising halogenated derivatives of the contaminants in the deactivated catalyst and a non-gaseous phase comprising non-volatile corrosion products. The amount of Lewis acid and/or Bronsted acid present in either phase is dependent upon the volatility of the particular acid components and the temperature and pressure of the regeneration zone. At least a portion of the regenerated catalyst containing one or more of the acid components may be recycled to a hydrocarbon conversion process.

DETAILED DESCRIPTION OF THE INVENTION

The hydrocarbon conversion ctalyst referred to herein comprises (a) one or more Lewis acids of the formula $MX_n$ where M is a component selected from the Group IIIA, IVB, V, VIB or VIII Elements of the Periodic Table or their mixtures, X is a halogen, n is the atomic ratio of halogen to M and varies from 1–8, preferably from 3–8, and (b) a strong Bronsted acid. For the purposes of this invention, X will be considered to be a single halogen even though it should be understood that X could refer to a mixed halogen such that $MX_n$ could be, for example, $TaF_4Cl$. The Periodic Table referred to is that described in "The Encyclopedia of Chemistry", Reinhold Publishing Corporation, 2nd Ed. (1966) at page 790. The term "elements" as used herein refers to the metals and metalloids of the aforementioned Groups of the Periodic Table.

Preferably, the catalyst system is composed of one or more Lewis acids and one Bronsted acid. Metal halides are preferred Lewis acids. Useful metal halide constituents include the chlorides and bromides of gallium, aluminum and iron and the fluorides, bromides and chlorides of titanium, vanadium, zirconium, niobium, tantalum, chromium, molybdenum, tungsten, arsenic, antimony and bismuth. Group IVB, V and VIB metal fluorides are preferred metal halides, Group V being most preferred. Specific examples of useful metal fluorides include antimony pentafluoride, tantalum pentafluoride, niobium pentafluoride, vanadium pentafluoride, tungsten hexafluoride, titanium tetrafluoride, molybdenum hexafluoride, bismuth pentafluoride, arsenic pentafluoride, mixtures thereof and the like. For the purposes of this invention, the fluorides, chlorides, and bromides of phosphorus, particularly phosphorus pentafluoride, and considered to be suitable metal halides. The most preferred metal halide catalyst constituents are tantalum and niobium halides, preferably tantalum pentafluoride, niobium pentafluoride and mixtures thereof. Tantalum pentafluoride is meant to include tantalum pentafluoride as well as its complex ions, e.g. ions such as $Ta_2F_{11}^-$, $Ta_3F_{16}^-$ and the like, that may be formed when tantalum pentafluoride is mixed with the Bronsted acid. This applies similarly to other metal halides.

The second component of the catalyst system is a Bronsted acid. Suitable Bronsted acids include a hydrogen halide, fluorosulfonic acid, trifluoromethanesulfonic acid, methanesulfonic acid, trifluoroacetic acid, sulfuric acid, phosphoric acid, fluorophosphoric acids, and the like. The Bronsted acid may also be admixed with a portion of its corresponding anhydride. The preferred Bronsted acid is a hydrogen halide. Useful hydrogen halides include hydrogen bromide, hydrogen chloride and hydrogen fluoride. The preferred hydrogen halide catalyst constituent is hydrogen fluoride. In general, when oxygen-containing Bronsted acids are employed, the acids should be separated from the metal halide component of the catalyst prior to regeneration in the presence of fluorine or chlorine. It is believed that such acids will undergo oxidation reactions with fluorine and, to a lesser extent, with chlorine, depending upon the severity of the operating conditions of the regeneration zone which can be determined by one skilled in the art.

The effectivness of the catalyst is related to the molar ratio of Bronsted acid to Lewis acid. While relatively minor amounts, i.e. less than equal molar amounts, of Bronsted acid relative to Lewis acid will dissolve at least a portion of the Lewis acid and thereby effect the reaction, the rate of reaction is inordinately slow. However, the reaction rate, i.e. the yield in a given period of time, will be increased if at least an equal molar amount of Bronsted acid relative to Lewis acid is present in the reaction zone. Increasing the mole ratio of Bronsted acid to Lewis acid provides additional Bronsted acid so as to dissolve more of the Lewis acid and thereby provide an increasing amount of liquid phase catalyst which will favor an increased reaction rate. The effect of increasing amounts of liquid phase catalyst on reaction rate becomes more pronounced when the mole ratio of Bronsted acid to Lewis acid is in excess of one and continues as the liquid phase of the catalyst increases. Thus, the mole ratio of Bronsted acid (hydrogen halide) to Lewis acid (metal halide) is preferably at least 2:1 and more preferably at least 5:1. The favorable effects mentioned above will ultimately level off as the Bronsted acid dilutes the acidity of the reaction system. Thus depending upon the relative amounts of catalyst constituents used, the catalyst, when no support is employed, may be a homogeneous solution of the Lewis acid in the Bronsted acid or a mixture of gaseous, solid, liquid and dissolved Lewis acid and Bronsted acid.

The catalyst may be used as the neat liquid, as a diluted solution or as a liquid adsorbed on a solid support. With regard to the use of the catalyst in solution, any diluent or solvent may be used that is inert to the catalyst under the particular hydrocarbon conversion reaction conditions. Typical diluents or solvents include sulfuryl chloridefluoride, sulfuryl fluoride, sulfolanes, polyfluorinated-polyhalogenated hydrocarbons, fluorinated hydrocarbons, Freons, mixtures thereof and the like. Hydrogen fluoride is the preferred reaction diluent when the Lewis acid portion of the catalyst system is a metal fluoride. When a solvent or diluent is used, sufficient amounts are employed to maintain the viscosity of the reaction mixture at a desired level. The amount of diluent employed can vary appreciably and can range as high as 98% volume of the reaction mixture. Typically, the diluent:catalyst volume ratio may range from 20:1 to 1:10. Higher dilutions may be desirable, for example, in those reactions that proceed with high exothermicity.

The catalyst system may be incorporated with a suitable solid carrier or support. Any solid catalyst support may be used that is inert to the catalyst under the reaction conditions. The support should be pretreated, such as by heating, chemical treatment or coating to remove substantially all water and/or hydroxylic or other basic sites that might be present. Reactive supports may be rendered inert by coating them with an inert material such as antimony trifluoride or aluminum trifluoride. Suitable solid supports include fluoride-treated or coated resins such as sulfonated cation exchange resins in the protonic form, fluoride treated acidic chalcites such as alumina, aluminosilicates, molecular sieves such as faujasite and zeolites, and acid-resistant materials such as graphite, chromosorb T, Fluoropak 80, charcoal, etc.

The supported catalyst can be prepared in any suitable manner, such as by conventional methods including dry mixing, coprecipitation or impregnation. In one embodiment, the supported catalyst is prepared by impregnating a suitable deactivated support with a Lewis acid such as tantalum pentafluoride and then with a Bronsted acid such as hydrogen fluoride.

In general, the partially deactivated catalyst may be derived from those reactions and side reactions that occur under the influence of Friedel-Craft's catalysts in, e.g., isomerization, alkylation, polymerization, cracking, hydrogenation, disproportionation and the like. The present invention is particularly applicable to isomerization and alkylation reactions. Typical isomerizable feedstocks include acyclic and alicyclic aliphatic hydrocarbons having at least four carbon atoms that are converted to a product enriched in an isomer thereof. Typically, acyclic hydrocarbons having at least four carbon atoms, that is straight chain or branched chain paraffins having from about 4 to 10 carbon atoms, preferably from about 4 to 8 carbon atoms, are converted to branched materials having higher octane ratings. Additionally, alicyclic hydrocarbons (naphthenes) having at least about 6 carbon atoms, typically from about 6 to 50 carbon atoms, preferably 6 to 15 carbon atoms, can be converted to isomers thereof by contacting the same with hydrogen in the presence of the catalyst system described previously. Mixtures of acyclic and alicyclic hydrocarbons can be used as the process feedstock. In a typical commercial operation, a paraffin stream containing mixtures of various types of open chain and closed chain paraffins is used as the process feedstock. Typical isomerization reaction conditions are summarized below.

| Range | Suitable | Preferred |
|---|---|---|
| Temperature, ° C | 0 – 150 | 30 – 75 |
| Hydrogen Partial Pressure, atm. | 0.1 – 140 | 0.3 – 25 |
| Reaction Time, min. | 0.5 – 1500 | 1 – 500 |
| Moles $H_2$/mole Hydrocarbon | 0.01 – 2.5 | 0.1 – 1.0 |
| Space Velocity, V/Hr./V | 0.05 – 200 | 0.25 – 20 |

In the alkylation of hydrocarbons with olefins, suitable olefinic starting materials are ethylene, propylene, butylenes, trimethylethylene and other isomeric pentanes, and similar higher monoolefinic hydrocarbons of either a straight chain or branched chain structure. Olefins containing 2 to about 12 carbons atoms per molecule are preferred while olefins containing 2 to 5 carbon atoms per molecule are particularly preferred. The reaction mixtures may also contain some amounts of diolefins. Although it is desirable from an economic viewpoint to use the normally gaseous olefins as reactants, normally liquid olefins may also be used. Thus, polymers, copolymers, interpolymers, crosspolymers, etc., of the above-mentioned olefins, as for example, propylene dimer, the diisobutylene and triisobutylene polymers, the codimer of normal and isobutylenes and the like may be used. The use of mixtures of two or more of the above-described olefins is also envisioned for this purpose.

Hydrocarbon feedstocks that are suitable for use in alkylation processes include paraffins, aromatic, alkyl substituted aromatic hydrocarbons and mixtures thereof. The paraffins as herein defined include the acyclic and alicyclic hydrocarbons. The acyclic hydrocarbons (straight and branched chain materials) contain at least 1, preferably 1 to about 12 carbon atoms per molecule, and may be exemplified by methane, ethane, propane, butanes, metmylbutanes, n-pentane, methylpentanes, methylhexanes, and the like. The alicyclic hydrocarbons (naphthenes) contain at least 5, typically from about 5 to about 15 carbon atoms per molecule, preferably 6 to 12 carbon atoms and may be exemplified by methylcyclopentane, dimethylcyclopentane, methylcyclohexane, ethylcyclohexzne, n-pentylcyclohexane and the like. Useful aromatic and alkyl aromatic hydrocarbons contain at least 6, preferably 6 to about 20 carbon atoms per molecule and are exemplified by benzene, ethyl benzene, n-butyl benzene and the like. Other acyclic or alicyclic hydrocarbons commonly found in conventional petroleum hydrocarbon light naphtha streams and the like may be present. Typical alkylation reaction conditions are summarized below.

| Range | Suitable | Preferred |
|---|---|---|
| Temperature, ° C | −100 − +150 | −10 − +80 |
| Hydrogen Partial Pressure, atm. | 0.1 − 100 | 0.3 − 25 |
| Reaction Time, min. | 0.001 − 60+ | 0.001 − 45 |
| Space Velocity based on olefin, V/Hr./V | 0.01 − 10 | 0.04 − 5 |

As the hydrocarbon conversion reaction proceeds, the activity of the catalyst system may decline. Some portions of said system may be deactivated so as to possess essentially no activity to catalyze the hydrocarbon conversion reaction while other portions may be only partially deactivated. While not wishing to be bound by any particular theory, it is believed that the present hydrocarbon conversion catalyst is deactivated or neutralized by contaminants which may be present in the hydrocarbon feedstock or which may be formed in situ during the hydrocarbon conversion reaction. The contaminants form complexes with the Lewis and/or Bronsted acid components of the catalyst system that are more stable, i.e. more catalytically inert, less acidic, i.e. more basic, and less catalytically active, than the Bronsted/Lewis acid complexes of the catalyst system. The complexes formed with the contaminants are substantially insoluble in the hydrocarbon phase and thus accumulate in the catalyst phase. As the complexes accumulate, the acidity of the catalyst is diminished, thereby decreasing the reactivity of the catalyst system. Both organic and inorganic contaminants can cause reduced activity of the present hydrocarbon conversion catalyst. Examples of inorganic materials that can cause the reduced activity are water, which may enter the reaction zone of the hydrocarbon conversion process in the feedstock or as the result of an operational mishap, and metal compounds which result from corrosion of the reaction zone internals or are present in heavier feedstocks. Examples of organic materials that can cause reduced activity are stable unsaturated ions, e.g., allylic ions, formed in situ during the hydrocarbon conversion reaction, nitrogen-containing compounds, sulfur and oxygen-containing compounds and the like. Thus it would be desirable that said feedstock, diluents and individual catalyst constituents be purified prior to use in the hydrocarbon conversion process to remove substantially all of the aforementioned contaminants in order to obtain maximum catalyst activity and catalyst life. By substantially is meant that the mole ratio of contaminants to Lewis acid is less than 1:2, preferably less than 1:4, and more preferably less than 1:10.

The level of reduced activity at which the catalyst should be regenerated is not only a matter of ability to catalyze the reaction but also a matter of economics. For example, it may be desirable to regenerate mildly deactivated catalyst to essentially fresh catalyst activity rather than allow the catalyst to be reduced to a much lower level of activity and be regenerated to fresh or to less than fresh activity. As used herein, the term "regeneration" or "regenerated" means recovering a catalyst that possesses a greater activity for hydrocarbon conversion than that possessed by the deactivated or partially deactivated catalyst. It should be understood that the regeneration process of the present invention is applicable to catalysts such as those defined above which have lost some degree of activity and that the regeneration may only partially restore the lost activity.

Although not necessary to the practice of the present invention, it may be desirable for economic reasons to separate at least a portion of the deactivated or partially deactivated catalyst from the hydrocarbon phase prior to regeneration. Preferably, substantially all of the hydrocarbon phase, i.e. all but that portion dissolved or otherwise entrained in the catalyst, is separated from the catalyst prior to regeneration. The separation may be accomplished by any suitable means including settling and decanting, volatilization and the like. The entrained or dissolved hydrocarbon feedstock can be stripped from the catalyst prior to regeneration. Residual hydrocarbon remaining in the catalyst will undergo reaction to form halogenated or partially halogenated hydrocarbons.

As mentioned above, in one embodiment of the present invention the deactivated or partially deactivated hydrocarbon conversion catalyst described herein is contacted with a halogen selected from the group consisting of fluorine or chlorine. In another embodiment of the present invention, when at least a portion of the catalyst has been converted to a metal oxyhalide or an oxide, the catalyst can be regenerated by direct halogenation as above or by hydrohalogenation using a hydrogen halide selected from the group consisting of hydrogen fluoride or hydrogen chloride followed by fluorination. The particular method chosen will depend upon process economics. Preferably, the hydrohalogen is hydrogen fluoride and the halogen or generated halogen is fluorine. If the halogen is fluorine, carbon, nitrogen, sulfur, oxygen-containing contaminants and allylic ions will be converted to more volatile fluorinated or partially fluorinated species. It is believed that water and any hydrolyzed catalyst species will be removed by conversion to a mixture of hydrogen fluoride, oxygen and oxyfluorides. However, when the halogen is chlorine, it is believed that only carbon contaminants will be removed by chemical reaction. If the hydrohalogen employed is hydrogen fluoride, the oxyhalide and oxide present will be converted essentially to water and metal fluoride, respectively. Hydrogen choride may also be employed and it is believed to behave in a manner similar to that of hydrogen fluoride. Although it is believed that some of the water may be removed from the catalyst by physical interaction with the hydrogen halide, the hydrohalogenated catalyst should then be contacted with fluorine to remove essentially all of the residual traces of water.

Thus, when the present catalyst system comprises fluoride compounds, the above-mentioned contaminants may be removed using fluorine. However, when chlorine is employed with fluoride catalysts, no undesirable exchange reaction will occur to consume the fluoride. When the catalyst system comprises chloride compounds, fluorine cannot be employed to regenerate the catalyst because fluorine will remove not only the organic and inorganic contaminants, but will convert the metal chloride to the corresponding metal fluoride. In the case of aluminum and gallium, however, the fluorides are not active. Thus, fluorides cannot be converted to chlorides by substitution reactions with chlorine or hydrogen chloride. However, chloride compounds are easily converted to fluoride compounds with fluorine or hydrogen fluoride. Therefore, fluorine and/or hydrogen fluoride are used as halogenating agents only when the catalyst comprises fluoride compounds, e.g., a metal fluoride and hydrogen fluoride. Chlorine and/or hydrogen chloride can be used as halogenating agents when the catalyst comprises fluoride or chloride compounds, e.g., a metal fluoride or chloride and hydrogen fluoride or chloride.

The halogens and hydrohalogens employed in the present invention are known articles of commerce and may be obtained as commercially available pure fluorine, chlorine, hydrogen fluoride and hydrogen chloride as well as being generated from various compounds. For example, fluorine can be derived from compounds such as chlorine trifluoride, bromine trifluoride, sulfur tetrafluoride and the like as well as from the electrolysis of hydrogen fluoride. Similarly chlorine may be obtained from compounds such as antimony pentachloride, sulfur chlorides, ferric chloride, sulfuryl chloride and the like. Hydrogen fluoride and hydrogen chloride may be generated from inorganic hydrofluorides and hydrochlorides, e.g., the corresponding alkali metal hydrohalides. Some of the halogen generating compounds such as chlorine trifluoride, bromine trifluoride, ferric chloride and sulfuryl chloride may be added to the regeneration zone. However, the generation of hydrogen halides from compounds such as potassium hydrofluoride should be external to the regeneration zone. Preferbly, the halogen or halogen generating agent entering the regeneration zone will be substantially anhydrous; i.e., will contain less than 5 mole %, preferably less than 3 mole %, and more preferably less than 1 mole % water. It may be desirable to dilute the halogen with an inert gas such as nitrogen, helium, argon and the like to dissipate the heat liberated during halogenation or hydrohalogenation reactions. In addition, since the halogenation and hydrohalogenation reactions are exothermic, the regeneration should be effected under conditions that will promote favorable temperature control.

The amount of halogen or hydrogen halide employed depends upon the amount and type of contaminants present in the deactivated or partially deactivated catalyst as well as the degree of reaction required to regenerate the catalyst, i.e. to separate the impurities from the Lewis acid alone or in combination with the Bronsted acid. Thus, the amount of halogen or hydrogen halide should be that sufficient to halogenate at least a portion of the contaminants such that the halogenated contaminants can be separated from at least the Lewis acid component of the catalyst. Thus, the contaminants may need be only partially halogenated. However, although not necessary to the practice of the present invention, it may be desirable to employ the halogen or hydrogen halide in an amount sufficient to satisfy the stoichiometry necessary for substantially complete halogenation of the contaminants. For example, when regenerating a partially deactivated catalyst comprising tantalum pentafluoride and hydrogen fluoride with fluorine, partial rather than complete fluorination of the organic contaminants could be sufficient i.e. forming partially fluorinated hydrocarbons, rather than complete stoichiometric reaction, e.g. forming carbon tetrafluoride. However, should any water be bound to the catalyst, substantially complete fluorination of the water would be required.

The temperature of the regeneration zone should be maintained at as low a level as possible in order to minimize undesirable side reactions, the excessive consumption of reagents, and further degradation of the hydrocarbon conversion catalyst. In general, the temperature will range from about $-30°$ C. to about $1000°$ C., more preferably from about $-30°$ to about $400°$ C.

The total pressure at which the regeneration is effected is not critical and will depend upon the extent of catalyst deactivation which, in turn, will depend upon the nature of the material being processed, the reaction diluent, if any, as will as other process variables. In general, total pressure will range from about 1 to about 100 atmospheres, preferably from about 1 to about 50 atmospheres, and most preferably from about 1 to about 35 atmospheres.

The regeneration occurs rather promptly and the contact time required need only be that sufficient to obtain a regenerated catalyst that possesses a greater activity for hydrocarbon conversion than that possessed by said deactivated or partially deactivated hydrocarbon conversion catalyst. Thus, the contact time may vary from a few seconds to several hours depending on the temperature and other inter-related variables. Generally, the contact time will vary from 1 second to about 5 hours, preferably from 1 second to about 2 hours, more preferably about 1 second to about 30 minutes.

The deactivated or partially deactivated catalyst may be regenerated in any suitable apparatus. Contacting may be effected in batch, multiple batch, semicontinuous, or continuous operation. For example, it may be carried out in continuous contacting equipment such as simple gravity operated contactors which no mechanical agitator, mechanically agitated contactors, centrifugal contactors, or packed or unpacked towers with or without mixing orifices. Preferably the contacting equipment is of appropriate design to insure good contact between the catalyst which is at least partially deactivated and the halogen-containing gas or hydrogen halide. Preferably, a high efficiency multistage contactor will be used. Equipment most suitable for a specific application can be selected by one skilled in the art. The contacting equipment does not require the use of any special materials of construction, i.e., carbon steel is quite satisfactory. However, alloy materials such as Carpenter 20 Cb-3 steel (Alloy 20), monel (Hastelloy C), aluminum 5052, aluminum 6061 and the like, as well as Teflon, may be required.

Thus when a deactivated or partially deactivated catalyst is regenerated according to the present invention, there results a gas phase comprising predominantly halogenated or partially halogenated derivatives of the contaminants present in said catalyst and a non-gaseous phase comprising corrosion products formed in the hydrocarbon conversion process, in the regeneration zone or in both. At least a portion of each phase may be recycled to the hydrocarbon conversion process. The gas phase, in addition to containing halogenated or partially halogenated derivatives of the contaminants present in the catalyst, may contain the Lewis acid and the Bronsted acid components of the catalyst of their mixtures. The amount of Bronsted and/or Lewis acid components present in the gas phase will vary depending upon the physical properties of the particular acids, i.e. volatility, a well as the temperature and pressure of the regeneration zone. The Bronsted and/or Lewis acid components may be recovered from the gas phase by several methods that would be obvious to one skilled in the art. For example, if the acid components were tantalum pentafluoride and hydrogen fluoride and sufficient amounts of tantalum pentafluoride were present in the gas phase to justify recovery, the acid components could be condensed therefrom. Preferably, at least a portion of the condensate is recycled to the hydrocarbon conversion process.

The non-gaseous phase may be solid, liquid or a mixture thereof depending upon the type of contaminants present in the deactivated or partially deactivated catalyst and on the operating conditions of the regeneration zone. The Lewis and/or Bronsted acid components not present in the gas phase will be present in the non-gaseous phase. At least a portion of the non-gaseous phase may be recycled to the hydrocarbon conversion process. Nonvolatile corrosion products, e.g. iron fluoride and any oxy-compounds, e.g. tantalum oxyfluoride formed through hydrolysis by adventitious water, may be present in homogeneous solution with the non-gaseous phase or as a separate solid phase. Preferably, the corrosion products are separated from the catalyst components therein prior to recycling the non-gaseous phase to the hydrocarbon conversion process. Solids which are present may be separated from the liquid portion of the non-gaseous phase by suitable mechanical means such as filtration or settling. If the non-volatile corrosion products and oxyfluorides are in homogeneous solution with the Lewis and/or Bronsted acid components of the catalyst and said component is volatile, e.g. tantalum pentafluoride or antimony pentafluoride, the heat generated during the regeneration could be sufficient to volatilize the acid component selectively, thereby effecting the simultaneous purification and separation of the acid component. Alternately, the acid components can be removed from the non-gaseous phase by simple distillation. It should be pointed out that there may be little if any corrosion products if the acid catalyst contacts a non-corrodible material such as Teflon, aluminum and the like. Thus when using such materials, depending upon the physical properties of the catalyst components as wekll as the temperature and pressure of the regeneration zone, there may be no non-gaseous residue.

The following examples are presented to further illustrate the process of the present invention and are not intended to unduly restrict the limits of the claims appended hereto.

EXAMPLE 1

Synthesis of tantalum pentafluoride from tantalum oxide using fluorine.

Tantalum oxide ($Ta_2O_5$) (9.8 g, 0.02 mole) was placed into a nickel boat 7 inches long, 0.67 inches wide, and 0.38 inches high. The boat was inserted into a Vycor glass tube (30 inches long with an outer diameter of 7/8 inches) are centered therein in the radial direction. The glass tube was then inserted into a 13 inch long 750 watt tube furnace such that the nickel boat was centered therein and one end of said tube was in contact with one end of the furnace, i.e. about 17 inches of the Vycor tube was not in contact with the furnace. Flurorine at atmospheric pressure was introduced into the glass tube at the end in contact with the furnace. Reaction between the fluorine and the oxide was initiated at about 50° C. as evidenced by the evolution of white vapors. The temperature increased to 250° C. via the heat released during the exothermic reaction and was subsequently maintained at that level by use of the furnace. About 20 minutes after the reaction was initiated, use of the furnace and the fluorine were discontinued since only a small residue of unreacted tantalum oxide (0.29 g.) remained in the boat. A white solid was observed to sublime onto the end of the glass tube not contacting the furnace. A sample (11.8 g) of the solid was scraped from the tube in a dry box under a nitrogen atmosphere into a tared Teflon bottle. The sample was analyzed and found to contain 65.72 wt. % tantalum and 33.95 wt. % fluorine and to have a melting point of 97°–98° C. The theoretical amount of tantalum and fluorine that should be present was calculated to be 65.57 wt. % and 34.42 wt. %, respectively. The melting point of tantalum pentafluoride is given as 96.8° C. in "The Handbood of Chemistry and Physics," CRC Press, 55th Ed. (1974–1975) at page B-144.

EXAMPLE 2

Regeneration of a substantially deactivated catalyst via conversion to tantalum oxide.

A hydrocarbon feedstock containing hexane (85 vol. %); cyclohexane (10 vol. %) and benzene (5 vol. %) was recycled, in the absence of hydrogen, three times over a catalyst comprising tantalum pentafluoride and hydrogen fluoride at 50° C. to deactivate the catalyst. The mole ratio of tantalum pentafluoride to hydrogen fluoride was about 1:10. When the activity was reduced by about 75%, the catalyst was stripped, at 40° C., of hydrogen fluoride and hydrocarbons, using a stream of nitrogen. A portion (8 g) of the substantially deactivated catalyst, i.e. a catalyst having a very low level of activity for hydrocarbon conversion, was quenched in hot water at about 80° C. The organic material was extracted with benzene and the remaining milky white aqueous suspension neutralized with hydrochloric acid and then dried overnight in an oven at 140° C. The white solid was extracted with water several times and dried again. A portion (2.0 g) of the white solid was then placed into a nickel boat, Vycor glass tube and tube furnace as in Example 1 and reacted with fluorine. The exothermic reaction was initiated at about 50° C. as in Example 1 and rose to 225° C. The furnace was used to maintain the temperature at that level for about four hours. The white solid thus formed on the wall of the glass tube, i.e. tantalum pentafluoride, melted between 95°–100° C.

EXAMPLE 3

Reaction of tantalum oxide with hydrogen fluoride.

tantalum oxide (10.0 g, 0.02 mole) was contacted with hydrogen fluoride (207 g., 10.5 mole) such that 8.2 g of the $Ta_2O_5$ was reacted. This resulted in the isolation of 6.3 g of a white crystalline product which, when analyzed was found to have a melting point between 164°–166° C. and to contain 55.82 wt. % tantalum, 32.14 wt. % fluorine, 1.17 wt. % hydrogen and 10.87 wt. % oxygen. A small sample (2.3 g) of the partially fluorinated product was placed into a nickel boat, Vycor glass tube and tube furnace as in Example 1 and contacted with fluorine at 50° C. to remove residual hydrogen and oxygen therefrom. By using the furnace, the temperature was increased to about 150° C. whereupon the reaction was initiated. The temperature was then increased from about 150° C. to about 275° C over a 2 hour period by the exothermic heat of reaction. Tantalum pentafluoride, a white solid, was observed to sublime onto the wall of the glass tube. This solid was found to have a melting point of 94°– 96.5° C.

EXAMPLE 4

Regeneration of a substantially deactivated catalyst with fluorine.

A catalyst containing tantalum pentafluoride and hydrogen fluoride in the mole ratio of about 1:10 was deactivated as described in Example 2 and then stripped of volatiles with nitrogen. The catalyst residue was analyzed and found to contain 10.65 wt. % carbon. A 6.3 g. sample of the residue was placed in a nickel boat, Vycor glass tube and tube furnace, and reacted with fluorine according to the procedure of Example 1. The exothermic reaction was initiated at a temperature of about 50° C. and was continued over a four hour period during which the temperature was increased to 175° C. The temperature was maintained at this level for another 1½ hours to insure completion of the reaction. 4.23 g of a white solid product, i.e. substantially pure tantalum pentafluoride, having a melting point between 94°–96.2°C. was obtained from the wall of the glass tube.

What is claimed is:

1. In a hydrocarbon conversion process which comprises contacting a hydrocabon feedstock with a substantially liquid phase catalyst comprising a metal fluoride selected from the group consisting of tantalum pentafluoride, niobium pentafluoride and mixtures thereof in combination with hydrogen fluoride, thereby forming a hydrocarbon phase and a catalyst phase, at least a portion of said catalyst phase having become deactivated due to the presence of organic contaminants and inorganic separating at least a portion of said catalyst phase from said hydrocarbon phase, the improvement which comprises regenerating at least a portion of said catalyst phase in a regeneration zone by contact therein with a halogen selected from the group consisting of fluorine or chlorine at a temperature between about −30° and about 1000° C. for a period of time sufficient to obtain a catalyst possessing a greater activity for hydrocarbon conversion than that possessed by the deactivated catalyst, at least a portion of said contaminants being converted to halogenated or partially halogenated hydrocarbons and volatilized during said regeneration.

2. The process of claim 1 wherein at least a portion of the hydrogen fluoride is distilled from the catalyst phase prior to regeneration.

3. The process of claim 2 wherein at least a portion of the metal fluoride component of the catalyst phase is recovered from the regeneration zone and recycled to said hydrocarbon conversion process.

4. The process of claim 1 wherein at least a portion of the catalyst obtained from the regeneration zone is recycled to the hydrocarbon conversion process.

5. The process of claim 1 wherein the regeneration is effected at a temperature ranging between −30° and 400° C.

6. The process of claim 1 wherein said hydrocarbon conversion process is isomerization and said hydrocarbon feedstock comprises an acyclic hydrocarbon having at least four carbon atoms, an alicyclic hydrocarbon having at least six carbon atoms and mixtures thereof.

7. The process of claim 1 wherein said hydrocarbon conversion process is alkylation and said hydrocarbon feedstock is selected from the group consisting of an acyclic hydrocarbon having at least one carbon atom, an alicyclic hydrocarbon having at least 5 carbon atoms, an aromatic and alkyl aromatic hydrocarbon having at least 6 carbon atoms and mixtures thereof and said hydrocarbon feedstock is reacted with olefins containing from 2 to about 12 carbon atoms per molecule.

8. In a hydrocarbon conversion process which comprises contacting a hydrocarbon feedstock with a substantially liquid phase catalyst comprising a metal fluoride selected from the group consisting of tantalum pentafluoride, niobium pentafluoride and mixtures thereof in combination with hydrogen fluoride, thereby forming a hydrocarbon phase and a catalyst phase, at least a portion of said catalyst phase having become deactivated due to the presence of organic contaminants and inorganic contaminants separating at least a portion of said catalyst phase from said hydrocarbon phase, the improvement which comprises regenerating at least a portion of said catalyst phase in a regeneration zone by contact therein with fluorine at a temperature in the range of from about −30° to about 1000° C for a period of time sufficient to obtain a catalyst possessing a greater activity for hydrocarbon conversion than that possessed by the deactivated catalyst, at least a portion of said contaminants being converted to halogenated or partially halogenated hydrocarbons and volatilized during said regeneration.

9. The process of claim 8 wherein said hydrocarbon conversion process is isomerization and said hydrocarbon feedstock comprises an acyclic hydrocarbon having at least four carbon atoms, an alicyclic hydrocarbon having at least six carbon atoms and mixtures thereof.

10. The process of claim 8 wherein said hydrocarbon conversion process is alkylation and said hydrocarbon feedstock comprises an acyclic hydrocarbon having at least one carbon atom, an alicyclic hydrocarbon having at least 5 carbon atoms, an aromatic and alkyl aromatic hydrocarbon having at least 6 carbon atoms and mixtures thereof and said hydrocarbon feedstock is reacted with olefins containing from 2 to about 12 carbon atoms per molecule.

11. The process of claim 8 wherein at least a portion of the catalyst obtained from the regeneration zone is recycled to the hydrocarbon conversion process.

12. The process of claim 8 wherein at least a portion of the hydrogen fluoride is distilled from the catalyst phase prior to regeneration.

13. The process of claim 12 wherein at least a portion of the metal fluoride component of the catalyst phase is recovered from the regeneration zone and recycled to said hydrocarbon conversion process.

14. The process of claim 8 wherein the regeneration zone is maintained at a temperature ranging from about −30° to about 400° C.

15. The process of claim 14 wherein at least a portion portion of the catalyst phase is hydrolyzed and is contacted with hydrogen fluoride or hydrogen chloride prior to contact with fluorine.

16. The process of claim 15 wherein said hydrocarbon conversion process is isomerization and said hydrocarbon feedstock comprises an acyclic hydrocarbon having at least four carbon atoms, an alicyclic hydrocarbon having at least six carbon atoms and mixtures thereof.

17. The process of claim 15 wherein said hydrocarbon conversion process is alkylation and said hydrocarbon feedstock is selected from the group consisting of an acyclic hydrocarbon having at least one carbon atom, an alicyclic hydrocarbon having at least 5 carbon atoms, an aromatic and alkyl aromatic hydrocarbon having at least 6 carbon atoms and mixtures thereof and said hydrocarbon feedstock is reacted with olefins containing from 2 to about 12 carbon atoms per molecule.

* * * * *